United States Patent [19]

Brunerie et al.

[11] Patent Number: 5,620,879

[45] Date of Patent: Apr. 15, 1997

[54] PROCESS FOR PRODUCING NATURAL CIS-3-HEXENOL FROM UNSATURATED FATTY ACIDS

[76] Inventors: Pascal Brunerie, 17 rue des Marais, 94440 Santeny; Yvette Koziet, 83 rue Beauregard, 94350 Villiers sur Marne, both of France

[21] Appl. No.: 497,146

[22] Filed: Jun. 30, 1995

[30] Foreign Application Priority Data

Jun. 8, 1995 [FR] France .................................. 95 06761

[51] Int. Cl.$^6$ .................................. C12P 7/02; C12P 7/24
[52] U.S. Cl. .................................. 435/155; 435/147; 435/192
[58] Field of Search .................................. 435/155, 147, 435/192

[56] References Cited

U.S. PATENT DOCUMENTS

| | | | |
|---|---|---|---|
| 4,769,243 | 9/1988 | Kanisawa et al. | 426/33 |
| 4,806,379 | 2/1989 | Goers et al. | 426/650 |
| 5,464,761 | 11/1995 | Muller et al. | 435/147 |

FOREIGN PATENT DOCUMENTS

| | | |
|---|---|---|
| 2652587 | 4/1991 | France . |
| WO-A-9324644 | 12/1993 | WIPO . |

OTHER PUBLICATIONS

Biotech Abs. 95–15887 Holtz et al WO9526413 Oct. 5, 1995.

*Primary Examiner*—Herbert J. Lilling
*Attorney, Agent, or Firm*—Dechert Price & Rhoads

[57] ABSTRACT

The present invention relates to a process for producing cis-3-hexen-1-ol from an unsaturated fatty acid, in which said synthesis is carried out from the latter by the combined action of a natural system of enzyme(s) allowing the oxidation of said fatty acid to cis-3-hexenal and of a yeast allowing the reduction of cis-3-hexenal to cis-3-hexenol in a culture medium. According to a first characteristic of the present invention, the enzymatic system consists of a plant mass obtained by grinding leaves harvested whole without predilacerating them. According to a second characteristic of the present invention, the enzymatic system is introduced in the form of a ground cellular product obtained by grinding followed by cell disintegration. Finally, advantageously, a reagent chosen from a ferrous cation, acetylsalicylic acid, chlorophyll B and the enzyme catalase, makes it possible to increase the yields of cis-3-hexenol.

13 Claims, 1 Drawing Sheet

Scheme for Producing Cis-3-Hexenol
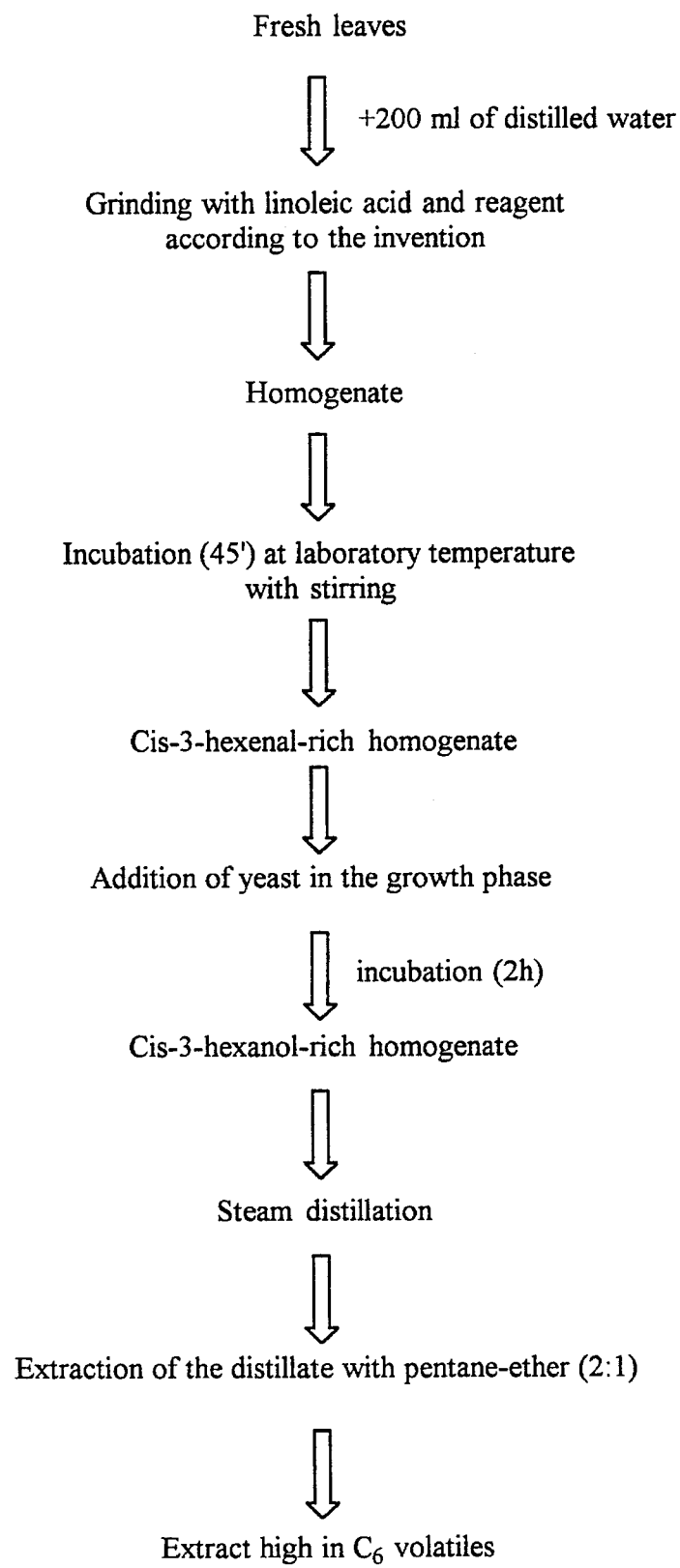

PROCESS FOR PRODUCING NATURAL CIS-3-HEXENOL FROM UNSATURATED FATTY ACIDS

The subject of the present invention is a process for producing cis-3-hexenol-1-ol from an unsaturated fatty acid. Its subject is more particularly a biological process for preparing the alcohol specified above.

Many $C_6$ aldehydes and alcohols are produced during the grinding of plant tissues and possess very valuable organoleptic and physiological properties. Among these compounds, cis-3-hexenol is widely used in flavoring compositions to give them a "fresh and green" note. The preparation of this alcohol is difficult, both by biological routes or by organic synthesis routes.

Many studies have been carried out to determine and measure the capacity of certain plant tissues to form cis-3-hexenol. Among these studies, there may be mentioned the study by Professor Peter Schreier which was the subject of the article (1986) "$C_6$ volatiles in homogenates from Green Leaves: localization of hydroperoxidase peroxidase lyase activity", Lebensm. Wiss. u. Technol. 19., 152–156. This study showed that many plant tissues, especially leaves, were capable of producing measurable quantities of cis-3-hexenol. More particularly, it was shown that radish and vine tops could produce up to 80 mg of cis-3-hexenol per kg of wet plant material. The abovementioned article gives the most widely accepted enzymatic pathway for passing from unsaturated fatty acids, especially from linoleic acid, to cis-3-hexenal and then to cis-3-hexenol. Thus, a lipoxygenase is thought to catalyze the formation of a hydroperoxide which is then thought to be opened by a hydroperoxide lyase to give the $C_6$ volatile aldehydes. An aldehyde reductase is then thought to allow the reduction of the aldehydes to the corresponding alcohol.

The abovementioned yields, although demonstrating the existence of an enzymatic system which makes it possible to manufacture cis-3-hexenol from unsaturated fatty acids, are insufficient to allow industrial exploitation.

That is the reason why it has been proposed to add to the ground leaf product linoleic acid, a natural precursor of $C_6$ aldehydes and alcohols, in order to increase the production of cis-3-hexenol and cis-3-hexenal.

U.S. Pat. Nos. 4,769,243 and 4,806,879 give a good illustration of such a technique. However, these techniques only allow a poor yield of desired alcohol.

French Patent 2,652,587 provides a process for synthesizing cis-3-hexenol which allows a significant improvement compared with the results obtained in the processes stated above.

In the process for synthesizing cis-3-hexenol described in FR 2,652,587, the synthesis is carried out starting with an unsaturated fatty acid, by the combined action of a natural system of enzyme(s) allowing the oxidation of said fatty acid to cis-3-hexenal and of a yeast allowing the reduction of cis-3-hexenal to cis-3-hexenal as indicated in scheme 1 below.

In this process, the addition of yeast makes it possible to promote the conversion of cis-3-hexenal to cis-3-hexenol rather than the isomerization of cis-3-hexenal to trans-2-hexenal. In addition, cis-3-hexenol is more stable than its aldehyde homolog and no isomerization to trans-2-hexenol is observed.

The aim of the present invention is to increase the yield of cis-3-hexenol by this process of production from unsaturated fatty acids by the combined action of a natural system of enzymes and yeasts.

It has been discovered according to the present invention that the yield was greatly increased by using an enzymatic system consisting of a ground plant product of leaves, especially of fennel leaves, harvested whole without predilacerating them.

The subject of the present invention is therefore a process for producing cis-3-hexen-1-ol from unsaturated fatty acids, in which said synthesis is carried out from the latter by the combined action of a natural system of enzyme(s) allowing the oxidation of said fatty acid to cis-3-hexenal and of a yeast allowing the reduction of cis-3-hexenal to cis-3-hexenol. According to a first characteristic of the present invention, the enzymatic system consists of a plant mass obtained by grinding leaves harvested whole without predilacerating them.

It has also been discovered that the quantity of cis-3-hexenol produced according to the process depends on the particle size of the ground product. If the ground product is a ground cellular product, the quantity of cis-3-hexenol produced is increased.

Advantageously, according to a second characteristic of the present invention, the enzymatic system is introduced in the form of a ground cellular product obtained by grinding followed by cell disintegration.

According to a third characteristic the present invention provides, in addition, reagents which can stimulate the enzymatic activities necessary for the production of cis-3-hexenol and/or inhibit secondary enzymatic activities responsible for metabolic leakages inducing a decrease in the yield of production of cis-3-hexenol.

It has indeed been discovered according to the present invention that the addition of a reagent chosen from a ferrous cation, acetylsalicylic acid, chlorophyll B and the enzyme catalase, makes it possible to increase the yields of cis-3-hexenol.

The subject of the present invention is therefore also a process for synthesizing cis-3-hexen-1-ol from an unsaturated fatty acid, in which said synthesis is carried out from the latter by the combined action of a natural system of enzyme(s) permitting the oxidation of said fatty acid to cis-3-hexenal and of a yeast permitting the reduction of cis-3-hexenal to cis-3-hexenol, wherein a reagent chosen from a ferrous cation, salicylic acid, chlorophyll B and the enzyme catalase is introduced with said unsaturated fatty acid and said enzymatic system into an aqueous culture medium.

The above mentioned first, second and third characteristics of the present invention can be used alone or in combination.

Advantageously, the addition of the reagents is done by the addition of the latter in water for diluting the plant material.

The ferrous cation may be in the form of ferrous salts, especially of a ferrous halide and in particular of ferrous chloride, but also of iron complexes such as porphyrins.

In the process according to the invention, the yeasts which are useful in the process may be any yeast having the following characteristics: a substantial alcohol dehydrogenase activity which makes it possible to reduce the carbonyl-containing compounds to the corresponding alcohols.

A yeast of the Saccharomyces type, preferably Saccharomyces cerevisiae, is advantageously used.

Advantageously, the reaction is carried out in a culture medium suitable for enzymatic systems and for yeasts. Culture media suitable for yeasts are well known to persons skilled in the art and need not be detailed in the present description.

It should however be noted that when ground leaf products are used as natural enzyme system, the pulp obtained by mixing said ground product in an aqueous medium constitutes an appropriate culture medium.

In order to carry out the process according to the present invention, it is desirable to carry out the following sequence of steps:

a) introduction of said unsaturated fatty acid and of said enzymatic system into an aqueous culture medium;

b) introduction of the yeast into said culture medium.

In order to minimize the production of undesirable compounds such as trans-2-hexenal and trans-2-hexenol, the introduction of said yeast should be carried out, at the latest, at the time when the cis-3-hexenal concentration in said medium is maximum.

As the curve of the cis-3-hexenal content as a function of time is a relatively flat curve, the period of time during which there is no great damage to be expected for adding the yeast is quite long. However, it is preferable to introduce the yeast simultaneously with the other reagents because the $C_6$ aldehydes and alcohols are formed very rapidly.

In order to obtain a better result, it is preferable that at the time of introducing the yeast into said culture medium, said yeast is in the growth phase. Advantageously, the pH of the culture medium is maintained between the round values 2 and 7, preferably between 3 and 6. The temperature at which the synthesis should take place is limited by the kinetics of the enzymatic systems and of the yeasts. In addition, from a certain rise in temperature, the yeasts are killed and can no longer be used. That is why, in general, a temperature of between 0° C. and 60° C. advantageously, between 15° C. and 40° C., in general in the region of room temperature, that is to say between 17° C. and 30° C., is used.

However, it may be advantageous to use the enzymatic system at temperature of between 0° C. and 20° C. in order to obtain an excellent selectivity for the production of derivatives of cis-3-hexene compared with those of trans-2-hexene. A significant decrease in temperature, although substantially reducing the kinetics, makes it possible to promote the formation of cis-3-hexenol compared with trans-2-hexenal and with trans-2-hexenol by preventing cis-3-hexenal from changing to the most thermodynamically stable product: trans-2-hexenal.

The enzymatic system which makes it possible to obtain a large quantity of $C_6$ volatiles can be obtained from a large number of plant tissues. Thus, it can be obtained from vine, tobacco, chicory (especially species producing endives), leeks, turnips, kohlrabi and radish leaves. Such systems also exist in the tissues of soybean, of rape and of different varieties of Rumex. The tissues of berry-producing plants such as the leaves of strawberry plants can also be mentioned. However, the preferred enzymatic system according to the present invention is that which can be obtained from fennel.

In general, these enzymatic systems use the constituent fatty acids which are capable of being converted to a $C_6$ aldehyde. It is however preferable to add some quantities of fatty acids as precursor in order to increase the yield. These fatty acids are in General linolenic or linoleic acids. This may also be any linear chain unsaturated fatty acid having at least three unsaturations, which unsaturations are situated in positions 6, 9 and 12 from the $CH_3$ end of the carbon chain.

When a plant mass obtained by Grinding suitable tissues is used as enzymatic system, it is advantageous that the fatty acid introduced has a concentration of between 0.1% and 2% by weight of the wet plant mass. The latter is in a 10% to 25% suspension in distilled water.

The fatty acids can be introduced in acid form or in the form of a salt in which the cation associated with the fatty acid is acceptable for the yeasts and for the enzymatic system. It is generally desirable that the fatty acid salts are soluble in aqueous media. The salts most commonly used are the salts of fatty acids with alkali metals and with the ammonium cation. Linolenic acid can be introduced either in a pure form, or mixed with other fatty acids. In particular, it is possible to use fatty acid mixtures obtained from the saponification of linolenic acid-rich oils, such as linseed oil. The saponification can be carried out either by the chemical route, or by the biological route, for example by means of lipases. There is appropriately used a linseed oil hydrolysate, especially at a concentration of 0.5% or 1% relative to the weight of the wet plant material used.

Other characteristics and advantages of the present invention will emerge in the light of the detailed description which will be Given below.

A. General operating Procedure (Scheme I)

1.50 g of fennel leaves (Foeniculum vulgate, variety vulgare) are Ground in a grinder and then suspended in 0.200 liter of water.

There are added simultaneously the additive tested and the linseed oil hydrolysate at 1% by weight relative to the weight of plant material used. The temperature is room temperature (about 20° C.). The yeasts are added at a concentration of 2% by weight relative to the plant material used. They are in the growth phase and are added simultaneously and in any case no later than after 45 min of incubation.

The homogenate obtained is adjusted to pH 4 and left stirring for 15 min. The homogenate is then distilled.

More specifically, the cis-3-hexenol produced is extracted from the ground product with the aid of a distillation column by steam distillation. The aqueous distillate collected is 40 times more concentrated than the original ground product. The distillate is extracted from the solvent and the extract is rectified.

2. The measurements were performed by gas chromatography according to the method described below.

The extraction and the assay of volatiles are performed according to the following procedure. After incubation, 200 ml of water and the internal standard are added to the medium. The medium is then subjected to steam distillation. 250 ml of distillate are recovered and extracted with three times 100 ml of pentane-ether (2:1). After drying and concentrating to 1 ml, the extract is analyzed by gas chromatography as described below:

Apparatus:

Hewlett Packard 5890 chromatograph equipped with a split/splitless injector and a flame ionization detector.

Column:

FFAP Hewlett Packard 50 m—diameter: 0.32 mm—thickness of the film: 0.52 µm.

Analysis conditions:

Column flow rate He: 2 ml/min, make up: 30 ml/min, air: 350 ml/min, hydrogen: 30 ml/min. Temperature of injector and detector: 250° C. Program 50° C. isotherm 3 minutes, 3° C./min up to 120° C., then 2° C./min up to 200° C., and isotherm at 220° C. for 60 minutes.

B. Optimization of the production of cis-3-hexenol

1) Addition of reagents

Using the above operating procedure, various tests were carried out in order to test various reagents which may have an influence on the production of cis-3-hexenal and of cis-3-hexenol by plant tissues. In addition, the influence of the reagent concentration was examined.

The data relating to the reagents selected according to the present invention are presented below in Tables I to IV.

Although the mechanisms of action of these various reagents are not completely elucidated in the production of cis-3-hexenol, it seems possible that the addition of the ferrous salt enhances the enzymatic activity because the lipoxygenases necessary for the production of the $C_6$ aldehydes and alcohols possess, in their active site, a (ferrous) iron atom linked to 4 imidazole rings derived from the 4 histidines, constituent amino acids of the enzyme, such that the reversible transition $Fe^{2+}$(ferrous)/$Fe^{3+}$(ferric) allows the exchanges of electrons necessary for the formation of the hydroperoxides.

The use of salicylic acid could inhibit the secondary metabolic pathway leading to the jasmone derivatives from the hydroperoxides produced by the lipoxygenase activity, and thus favor the pathway leading to the $C_6$ alcohols and aldehydes.

The addition of chlorophyll B could be involved in the chain of enzymatic reactions leading from the unsaturated fatty acids to the $C_6$ aldehydes and alcohols, making it possible to increase the enzymatic activity.

Catalase is an enzyme known to form water and oxygen from hydrogen peroxide ($H_2O_2$). This compound is a by-product of the enzymatic activity involved in the oxidation of unsaturated fatty acids and inhibits the enzymatic activity. The addition of catalase to the ground plant product could therefore allow us to remove the inhibition and thus promote the activity of the enzymes of interest.

From the examination of the results, it appears that for certain reagents, there is an optimum quantity which can be determined, depending on the relevant enzymatic systems, by simple operating procedures.

Thus, the concentration of ferrous salt should be greater than 1 mM in the ground plant product.

The concentration of salicylic acid may range from 0.5 to 1.5 mM in the ground plant product.

The concentration of chlorophyll B is advantageously greater than $5 \times 10^{-6}$ mM in the ground plant product.

Finally, the concentration of catalase in the ground plant product is advantageously greater than 5,000 units of enzymatic activity per liter of ground product.

The results obtained are the following:

a) Ferrous chloride (FeCl$_2$)

TABLE I

| | | |
|---|---|---|
| FeCl$_2$ (concentration expressed in millimolar in the ground plant product) | 1 | 2 |
| Concentration of cis-3-hexenol in ppm in relation to fennel | 327 | 302 |
| Control without FeCl$_2$ | 342 | 281 |
| Δ in % | −15% | +7.5% | b) Acetylsalicylic acid

TABLE II

| | | | | |
|---|---|---|---|---|
| Acetylsalicylic acid (concentration expressed in millimolar in the ground product) | 0.25 | 0.5 | 1 | 2 |
| Concentration of cis-3-hexenol in ppm in relation to fennel | 310 | 325 | 425 | 295 |
| Control without reagent | 342 | 81 | 342 | 342 |
| Δ in % | −10 | +16 | +24 | −14 | c) Chlorophyll B

TABLE III

| | | |
|---|---|---|
| Chlorophyll B in mg per 50 g of fennel | 1 | 2 |
| Concentration of cis-3-hexenol in ppm in relation to fennel | 346 | 417 |
| Control without reagent | 342 | 342 |
| Δ in % | +1 | +22 |

The chlorophyll B concentrations are $4.4 \times 10^{-6}$ and $8.8 \times 10^{-6}$ millimolar respectively (MW=907.51). d) Catalase

TABLE IV

| | | |
|---|---|---|
| Catalase in mg per 50 g of fennel | 10 | 100 |
| Concentration of cis-3-hexenol in ppm in relation to fennel | 377 | 412 |
| Control without catalase | 342 | 342 |
| Δ in % | +10 | +20 |

These concentrations of 10 mg per 50 g of fennel and 100 mg per 50 g of fennel correspond to 6,160 and 12,320 units of enzymatic activity per liter of ground product, respectively.

In Tables I to IV, the concentration of cis-3-hexenol is expressed in ppm relative to the mass of ground fennel plant product.

2) Influence of the grinding on its expression (fennel: Foeniculum vulgare variety vulgare)

It is not possible to give a particle size range to characterize the fineness of the ground product, the latter being very heterogeneous. It indeed contains many fibers of different sizes which make measurements of particle size inconsistent. In contrast, the various tests carried out unambiguously show the critical influence of the nature of the grinding.

| | Batch 1 | Batch 2 | Batch 3 | Mean |
|---|---|---|---|---|
| % leaves | 38 | 31 | 27 | 32 |
| A = 2 grindings with a hammer mill | 360 | 307 | — | |
| B = only 1 grinding with a hammer mill + 1 grinding using a cell disintegrator | — | — | 350 | |
| C = 2 grindings with a hammer mill + 1 grinding using a cell disintegrator | 417 | 387 | 364 | 389 |

The 389 ppm potential in the whole plant (which corresponds to 1,215 ppm in the leaf obtained in experiment C) shows that the initial grinding is not limiting.

The second grinding is limiting with the hammer mill, but the maximum yield is achieved only with the cell disintegrator.

The hammer mill used is a RIETZ RD 12 type hammer mill and the cell disintegrator is of the single rotor SILVERSON 600 LS type.

3) Effect of the harvesting mode on the yield

| Whole plant | Portable silage cutter | Self-propelled silage cutter |
|---|---|---|
| 389 ppm | 216 ppm | 290 ppm |

The silage cutter cuts the plant into small pieces. The silage cutter makes it possible to harvest the plant material preground. This therefore causes a substantial trauma, thus decreasing the enzymatic activity. The maximum yield is obtained with the whole plant.

We claim:

1. A process for producing cis-3-hexenol-1-ol from an unsaturated fatty acid that is convertable to a cis-3-hexenal via a plant-derived metabolic pathway, the process comprising the steps of, in a culture medium, (a) converting the fatty to cis-3-hexenal by contacting the fatty acid with a natural system of enzyme(s), said system consisting of a ground plant mass obtained by grinding and cell disintegration of leaves harvested whole without predilacerating them, wherein said leaves comprise enzyme(s) suitable for converting the fatty acid to cis-3-hexenal, and (b) converting cis-3-hexenal to cis-3-hexenol by contacting the cis-3-hexenal with a yeast comprising an alcohol dehydrogenase suitable for converting cis-3-hexenal to cis-3-hexenol.

2. A process for producing cis-3-hexenol-1-ol from an unsaturated fatty acid that is convertable to a cis-3-hexenal enzymatically, the process comprising the steps of, in a culture medium, (a) converting the fatty acid to cis-3-hexenal by contacting the fatty acid with a system of enzyme(s) suitable for converting the fatty acid to cis-3-hexenal and (b) converting cis-3-hexenal to cis-3-hexenol by contacting the cis-3-hexenal with a yeast comprising an alcohol dehydrogenase suitable for converting cis-3-hexenal to cis-3-hexenol, wherein a reagent, chosen from the group consisting of (i) a ferrous cation, (II) salicylic acid, (II) chlorophyll B and (iv) the enzyme catalase, is introduced with the unsaturated fatty acid and the enzymatic system into the culture medium.

3. The process as claimed in one of "claims 1 and 2", wherein the enzymatic system is introduced to the culture medium in the form of fennel leaves.

4. The process as claimed in claim 2, wherein the enzyme system is a ground plant mass and the reagent is added to the ground plant mass.

5. The process as claimed in one of "claims 1 and 2", wherein the introduction of the yeast into the culture medium is carried out no later than the time when the cis-3-hexenal concentration in the medium is maximum.

6. The synthesis process as claimed in claim 2, wherein at the time of the introduction into the culture medium, the yeast is in the growth phase.

7. The process as claimed in one of "claims 1 and 2", wherein the pH of the culture medium is maintained between 2 and 7.

8. The process as claimed in claims 7, wherein the pH of the culture medium is maintained between 3 and 6.

9. The process as claimed in one of "claims 1 and 2", wherein the temperature of the culture medium is maintained between 15° C. and 40° C.

10. The process as claimed in one of "claims 1 and 2", wherein the fatty acid is linolenic acid.

11. The process as claimed in claim 10, wherein the fatty acid is introduced into the culture medium at a concentration of between 0.1% and 2% by weight of the plant mass.

12. The process as claimed in claim 4, wherein the linolenic fatty acid is introduced into the culture medium in the form of linseed oil hydrolysate.

13. The process as claimed in one of "claims 1 and 2", wherein the cis-3-hexon-1-ol is recovered by steam distillation.

* * * * *